United States Patent [19]

Horlenko et al.

[11] 4,156,633

[45] May 29, 1979

[54] ACRYLIC ACID PURIFICATION

[75] Inventors: Theodore Horlenko; Gene J. Fisher, both of Corpus Christi, Tex.

[73] Assignee: Celanese Corporation, New York, N.Y.

[21] Appl. No.: 709,841

[22] Filed: Jul. 29, 1976

Related U.S. Application Data

[63] Continuation of Ser. No. 512,643, Oct. 7, 1974, abandoned.

[51] Int. Cl.² ............... B01D 3/34; C07C 51/44; C07C 57/04
[52] U.S. Cl. ........................... 203/93; 203/42; 203/97; 203/98; 203/87; 203/DIG. 21; 203/DIG. 25; 55/84; 562/600
[58] Field of Search ............ 203/42, 97, 98, 96, 203/95, DIG. 21, 87, 91, 92, 93, 94, DIG. 25; 55/84; 202/153; 260/526 N

[56] References Cited

U.S. PATENT DOCUMENTS

| | | | |
|---|---|---|---|
| 3,002,017 | 9/1961 | Wearsch et al. | 260/526 N |
| 3,113,851 | 12/1963 | Fukita et al. | 203/42 |
| 3,405,172 | 10/1968 | Brown et al. | 260/530 |
| 3,555,082 | 1/1971 | Sennewald et al. | 260/526 N |
| 3,868,417 | 2/1975 | Duembgen et al. | 260/526 N |

*Primary Examiner*—Wilbur L. Bascomb, Jr.
*Attorney, Agent, or Firm*—Stewart N. Rice; Ralph M. Pritchett

[57] ABSTRACT

Acrolein and other light ends are removed from the effluent of a process for the production of acrylic acid by the vapor phase catalytic oxidation of acrolein or an acrolein precursor, such as propylene, by passing the effluent to the base of a fractionation tower and contacting such with the descending stream of liquid within the tower so as to partially condense the condensibles in the effluent, a portion of the liquid bottoms being recycled to the upper portions of the tower and a portion withdrawn as crude acrylic acid product. Acrolein is removed overhead.

12 Claims, 1 Drawing Figure

ACRYLIC ACID PURIFICATION

This is a continuation, of application Ser. No. 512,643, filed Oct. 7, 1974 and now abandoned.

BACKGROUND OF INVENTION

Processes for the production of acrylic acid by vapor phase catalytic oxidation of acrolein and acrolein precursors, such as allyl alcohol and propylene, are well known in the prior art. For example processes for such are disclosed in U.S. Pat. No. 3,065,264, issued Nov. 20, 1962 to Theadore A. Koch et al and in U.S. Pat. No. 3,405,172, issued Oct. 8, 1968 to Christopher J. Brown, et al. Such processes involve passing acrolein or an acrolein precursor, that is a compound which gives rise to acrolein under the reaction conditions, over an oxidation catalyst at an elevated temperature, water being present in the feed in some instances. High conversions to acrylic acid are obtained, however, the reactor effluent will contain some acrolein which (along with other compounds) needs to be separated from the acrylic acid monomer. It is desirable to both rapidly cool the reaction product and to rapidly remove any acrolein present. The rapid cooling seems to prevent polymer formation while the rapid removal of acrolein is critical in eliminating acrolein contamination in the downstream acrylic acid recovery system. A rapid quench such as that disclosed in U.S. Pat. No. 3,405,172, referred to above, has been used to accomplish such. These rapid quench systems operate so as to immediately condense essentially all of the condensibles in the reactor effluent, but have been found to be undesirable in that in such systems the acrolein unduly reacts with the water present to form hydroxypropionaldehyde or reacts with itself to form oligomers. These products will later decompose back to form acrolein downstream in the distillation towers of an acrylic acid recovery system and contaminate the acrylic acid product.

SUMMARY

It is thus an object of the present invention to provide a new method for treating the effluent from the vapor phase catalytic oxidation of acrolein or an acrolein precursor so as to accomplish rapid removal of acrolein therefrom. It is a particular object of the present invention to provide a method for treating the effluent from the vapor phase catalytic oxidation of propylene in the presence of water so as to rapidly remove acrolein therefrom. Additionally, the present invention also accomplishes the object of removing light ends other than acrolein from such an effluent. Additional objects will become apparent from the following description of the present invention.

The foregoing and other objects are accomplished by the present invention which in one of its aspects is a method for recovery of a crude acrylic acid from the effluent gas derived from the vapor phase catalytic oxidation of acrolein or an acrolein precursor so as to produce acrylic acid, and which effluent gas contains acrolein, which method comprises passing the effluent gas at a temperature of from 100° to 300° C. to the base of a fractionation tower where said effluent gas is intimately contacted with a descending stream of liquid in said fractionation tower, removing a liquid bottoms stream from the bottom of said fractionation tower, withdrawing a portion of said liquid bottoms stream as a crude acrylic acid containing condensate, recycling the remainder of said liquid bottoms stream as a liquid recycle to the upper portions of said fractionation tower, and removing overhead vapors from said fractionation tower comprising acrolein, said stream of liquid which is intimately contacted with said effluent being at a temperature which is within 15 Centigrade degrees but does not exceed the dew point of said effluent gas at the pressure maintained in the bottom of said fractionation tower, the said overhead vapors being withdrawn from said fractionation tower at a temperature within the range of 0° to 40° C., and the said liquid recycle having been cooled to a temperature substantially less than the temperature of said liquid bottoms stream when removed from the bottom of said fractionation tower.

DETAILED DESCRIPTION OF THE INVENTION

Figure 1:
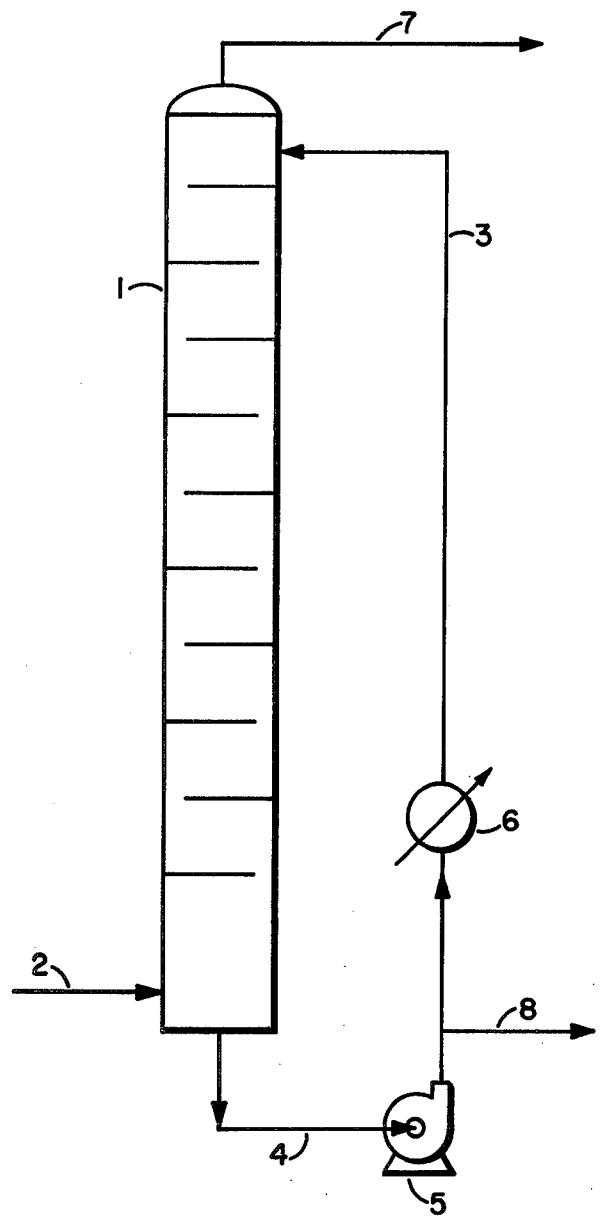
FIG. 1 is a schematic diagram of the use of a fractionation tower to accomplish the present invention.

The present invention may be applied to treat the effluent of the various processes wherein acrylic acid is produced by vapor phase catalytic oxidation of acrolein or an acrolein precursor. The particular method utilized for the vapor phase catalytic oxidation is not particularly critical to the present invention and will not be dealt with in detail herein. Generally speaking, the vapor phase catalytic oxidation is accomplished at an elevated temperature between about 300° C. and 500° C. and pressures ranging from atmospheric up to about 20 atmospheres, although a substantially atmospheric pressure is preferred and usually used. It is preferrable to pass a diluent to the oxidation reactor along with the feed, which diluent is inert under the oxidation reaction conditions. The diluent will usually be present so as to comprise from about 10 to 90% by volume of the reactor feed. Examples of diluents utilized in various processes are nitrogen, propane, butane, carbon dioxide, water, and mixtures of such. The particular diluent used will vary according to the feed material, catalyst, and the like, with water being preferred in most instances. The presence of water is especially preferred when propylene is the material being oxidized to acrylic acid.

Catalysts used in the vapor phase oxidation generally contain compounds of molybdenum and oxygen together with one or more other polyvalent compounds such as silicon, phosophorous, chromium, vanadium, iron, cerium, titanium, nickel, tungsten, bismuth, tin, antimony, cobalt, beryllium, zirconium, and uranium. The catalyst may thus be the molybdates of such molybdenum and such polyvalent compounds or mixtures of molybdenum oxide and the oxides of the polyvalent compounds. The catalyst may be employed in static or fluidized bed form. Contact times may vary widely, depending upon the particular catalyst used, for example from 0.2 to 20 seconds.

The effluent from the vapor phase catalytic oxidation will contain a mixture of compounds in addition to the desired acrylic acid monomer. In addition to the acrylic acid there will be present minor amounts of acrolein (usually from 0.05 to 1.0% by volume). There will also be present the water and carbon oxides formed as by-products in the oxidation reaction, the nitrogen from air where air is used as the source of oxygen in the oxidation reaction, and the inert diluent utilized that may also be water, nitrogen or carbon oxides as pointed out above. Usually there will also be present minor amounts of other impurities formed in the oxidation reaction zone such as acetic acid, propionic acid, acetaldehyde and formaldehyde. Many of the components in the effluent are considered as noncondensibles since at normal temperature and pressure, that is at 20° C. and atmospheric pressure, they do not exist as liquids; for example the carbon oxides formed as by-products as well as any impurity or diluent in the feed to the vapor phase catalytic oxidation reactor which is normally gaseous. These may hereafter sometimes be referred to as non-condensibles, while the other portions of the effluent such as acrylic acid, acrolein and water may be referred to as condensibles. The process is best suited for treating those effluents derived from a vapor phase catalytic oxidation wherein water was used as a diluent. These effluents will generally contain by volume from about 0.05 to 1.0% acrolein, 2 to 10% acrylic acid, 40 to 60% water, 35 to 55% non-condensibles such as nitrogen and carbon oxides and propylene but mainly nitrogen, and 0.1 to 2% miscellaneous hydrocarbons and oxygenated hydrocarbons other than acrolein and acrylic acid, such as acetic acid, formaldehyde, and the like.

Referring now to FIG. 1 for a more detailed explanation of the present invention, to the base of a fractionation tower 1, there is passed through line 2 the effluent from the vapor phase catalytic oxidation zone. In the base of tower 1 the effluent from line 2 is intimately contacted with the descending liquid within tower 1, that is the liquid on or from the first tray, such that a portion of the condensibles are condensed to liquid while the remainder of the condensibles and all of the noncondensibles begin to ascend the fractionation tower in the form of a vapor. This differs from the usual quench system where all, as opposed to a portion, of the condensibles are condensed to liquid immediately upon contact with a quench liquid.

The fractionation tower may be of conventional design and may contain trays or packing, although trays are preferrable. When trays are utilized, any of the conventional trays, such as sieve trays and bubble-cap trays may be used. Packed tower may include packing such as Berl saddles or Raschig rings. The fractionation tower should generally contain the equivalent of at least 3 theoretical trays, and in actual practice the fractionation tower should contain from 5 to 20 actual trays.

Still referring to FIG. 1, the feed from line 2 should enter below the first tray or below the packing where a packed tower is used. There is passed to the top of tower 1 through line 3 a portion of the liquid removed as liquid bottoms stream through line 4. Such liquid bottoms stream is pumped by pump 5, a portion then withdrawn as crude acrylic acid product through line 8 with the remaining portion being that passed as a liquid recycle to the top of the tower through line 3 after being cooled to a temperature substantially less than the liquid bottoms stream, that is at least 20° C. less, in cooler 6. Of the total liquid bottoms stream removed through line 4, about 10 to 20% should be withdrawn as crude acrylic acid product through line 8 and the remaining 80 to 90% used as liquid recycle, which will be passed to upper portions of the fractionation tower. Actually the point of removal of the crude acrylic acid product from the liquid bottoms stream is not critical and may be accomplished either before or after cooling, depending on the desired temperature of the crude acrylic acid.

Fractionation tower 1 is preferrably operated at a pressure within the range of 600 to 1600 millimeters Hg. absolute. Either higher or lower pressures may be used, but because of economic considerations, such will not generally be practical. The pressure at the base of the tower will be greater than that at the top by an amount sufficient to overcome the hydraulic pressure of the liquid descending the column plus the pressure drop due to vapor velocity. In order to achieve the benefits of the present invention, tower 1 must be operated such that the temperature of the liquid which contacts the effluent gas being passed through line 2 does not exceed, but is within 15° C. of the dew point of such effluent. This will be the liquid on the first tray of a distillation tower having trays, or, in case of a distillation tower having packing will be the liquid at the bottom of the bed of packing. Theoretically the liquid should be at the dew point for most efficient operation, but in actual practice a temperature about 1° to 5° C. below the dew point of the tower feed should be maintained. The dew point of the effluent of the vapor phase catalytic oxidation will, of course, vary according to its composition. In processes wherein propylene is oxidized to acrylic acid in the presence of a water diluent, the dew point will usually be within the range of 90° to 95° C. at 1000 millimeters mercury absolute.

The operation of tower 1 should also be such that the overheads, that is the vapor stream removed from the top of tower 1 through line 7, should be at a temperature within the range of 0° to 40° C., preferably 24° to 35° C., with higher temperatures resulting in undue acrylic acid losses. In order to achieve the desired overhead vapor temperature, the liquid passed to the top of tower 1 should be cooled to a temperature lower than that of such overhead vapor removed through line 7, more particularly about 7° to 25° C. lower will usually suffice. It is not necessary that all the portion of the liquid bottoms stream which is recycled through line 3 be passed to the top of tower 1. For example, excellent results may be obtained, with less cooling of the liquid recycle required, by passing a portion of the liquid recycle to a point or points in the upper half of the tower but below the top of the tower, with the remainder being passed to the top of the tower. If the liquid recycle is split, then it is recommended that at least 10% thereof be passed to the top of the tower, for example from 10 to 50% to the top, and the remainder passed to one or more points in the upper half of the tower. An especially suitable scheme involves passing from 10 to 20% of the liquid recycle to the top of the tower with from 80 to 90% being passed to the upper half, more preferrably approximately two-thirds up the tower, after being cooled to a temperature of from 35° to 60° C.

When operating according to the invention, practically all of the non-condensibles in the effluent from the vapor phase catalytic oxidation will appear in the overheads of the fractionation tower as will most of the acrolein present. The bottoms stream removed through line 4 will comprise mainly a crude acrylic acid product which contains most of the water, if any, in the system.

EXAMPLE I

The effluent from a vapor phase oxidation of propylene utilizing a commercially available molybdenum oxide containing catalyst was treated in an apparatus as illustrated in FIG. 1. Fractionation tower 1 consisted of a 3 inch Oldershaw column having 5 sieve trays. Liquid holdup per tray was 40 ml. During the run the overhead pressure was maintained at 978 mm Hg. and the pressure at the base of the tower maintained at 988 mm Hg. Overhead vapor temperature was maintained at 29° C., the liquid removed from the base was maintained at 90° C. and the liquid on the first tray maintained at 90° C. Temperature of the feed through line 2 was about 160° C. and the dew point of such feed at the base pressure was about 90° C. About 7000 grams per hour of liquid cooled to 19° C. was recycled through line 3 to the top of tower 1.

The effluent of the vapor phase catalytic oxidation zone fed through line 2 consisted of about 27.1 moles/hour of non-condensibles (mostly nitrogen), 0.0315 moles/hour acrolein, 2.725 moles/hour acrylic acid, 35.416 moles/hour water, and 0.545 moles per hour miscellaneous oxygenated hydrocarbon by-products. The overhead vapors consisted of about 27.1 moles/hour of non-condensibles, 0.030 moles/hour of acrolein, 0.024 moles/hour of acrylic acid, 0.683 moles/hour of water, and 0.006 moles/hour miscellaneous oxygenated hydrocarbons. The base liquid comprised about 0.0015 moles per hour acrolein, 2.701 moles/hour acrylic acid, 34.73 moles/hour water and 0.539 moles/hour miscellaneous oxygenated hydrocarbons. Thus over 95% of the acrolein was removed with only 0.9% of the acrylic acid lost in the overhead.

EXAMPLE II

The effluent from the vapor phase oxidation of propylene substantially of the composition of that of Example I was treated in a pilot plant distillation tower having 10 seive trays. The distillation tower was operated such that the overhead vapor temperature was 29° C., the liquid off the top tray was 20° C. and the liquid bottoms residue stream was 88° C. Overhead pressure was maintained at about 890 mm Hg. absolute and bottoms pressure was about 965 mm Hg. absolute. About 120 pounds per hour of the oxidation effluent at 195° C. was passed to the base of the tower and about 63 pounds per hour of vapors were removed as overheads. The liquid bottoms stream of 812 pounds per hour was first cooled from 88° C. to 46° C. by use of cooling water and then 57 pounds per hour removed as crude acrylic acid product; and the remaining 755 pounds per hour recycled. Of the 755 pounds per hour recycled, 655 pounds per hour was fed without further cooling onto the eighth tray from the bottom, while the remaining 100 pounds per hour was further cooled to 10° C. and then fed onto the top tray. Acrylic acid losses amounted to about 1.9% with about 91% of the acrolein being removed in the overhead vapors.

The above examples illustrate treatment of an oxidation effluent wherein water was used as a diluent however the process may be applied to those wherein a non-acqueous diluent is used. In such cases, without departing from the present invention, it will usually be desirable to cut down on acrylic acid losses by the introduction of fresh liquid water to the top of the distillation tower, the water being in addition to the recycle stream. Water addition serves to reduce the concentration of acrylic acid on the tray and thus reduce the acrylic acid concentration in the overhead vapors. Even when water is used as the diluent in the oxidation reactor such that large amounts are present in the feed to the distillation tower, additional water may be added to the top tray in order to decrease acrylic acid losses, although such might not be desirable from an economical standpoint. When water is introduced onto the top tray it will usually be in amounts of less than 50% by weight e.g. 5 to 50%, of the stream being recycled from the liquid bottoms stream.

The embodiments of the invention in which an exclusive property or privilege is claimed are defined as follows:

1. A method for the separation of a crude acrylic acid from the effluent gas derived from the vapor phase catalytic oxidation of acrolein or an acrolein precursor so as to produce acrylic acid and which effluent contains acrolein, which method comprises passing said effluent gas at a temperature of from 100° to 300° C. to the base of a fractionation tower where said effluent gas is intimately contacted with a descending stream of liquid in said fractionation tower, removing a liquid bottoms stream comprising predominantly crude acrylic acid and water from the bottom of said fractionation tower and withdrawing a portion of said liquid bottoms stream as crude acrylic acid containing condensate, recycling the remainder of said liquid bottoms stream as a liquid recycle to upper portions of said fractionation tower, and removing overhead vapors from said fractionation tower comprising a predominant portion of the acrolein contained in said effluent gas; said descending stream of liquid which is intimately contacted with said effluent gas being at a temperature which is within 15 Centigrade degrees but does not exceed the dew point of said effluent gas at the pressure maintained at the base of said fractionation tower, said overhead vapors being withdrawn from said fractionation tower at a temperature within the range of from 0° to 40° C., and the said liquid recycle being at a temperature substantially less than the temperature of said liquid bottoms stream.

2. The method of claim 1 wherein said effluent gas is derived from the vapor phase catalytic oxidation of propylene in the presence of water as a diluent.

3. The method of claim 2 wherein said fractionation tower is operated at a pressure within the range of from about 600 to 1600 millimeters mercury absolute.

4. The process of claim 3 wherein substantially all of said liquid recycle is recycled and introduced to the top of said fractionation tower.

5. The method of claim 3 wherein of said liquid recycle, at least 10% of said liquid recycle is introduced at the top of said tower.

6. The method of claim 5 wherein from 10 to 50% of such liquid recycle is introduced at the top of said fractionation tower after being cooled to a temperature which is from 7° to 25° C. lower than the temperature of the overhead vapors, and wherein the remaining 50 to 90% of said liquid recycle is passed to one or more points in the upper half of said tower but below the top thereof after being cooled to a temperature of from 35° to 60° C.

7. The method of claim 3 wherein said effluent gas consists essentially of, by volume, from 40 to 60% of water, 2 to 10% of acrylic acid, 0.05 to 1.0% of acrolein, 35 to 55% of normally gaseous non-condensibles and 0.1 to 2.0% miscellaneous hydrocarbons and oxygenated derivitives thereof other than acrolein and acrylic acid.

8. The method of claim 3 wherein liquid water is introduced onto the top tray of said fractionation tower.

9. The method of claim 4 wherein liquid water is introduced onto the top tray of said fractionation tower.

10. The method of claim 6 wherein liquid water is introduced onto the top tray of said fractionation tower.

11. The method of claim 1 wherein liquid water in an amount which is from 5 to 50% by weight of said liquid recycle is introduced onto the top tray of said fractionation tower.

12. A method for separating a crude acrylic acid product from the effluent gas derived from the vapor phase catalytic oxidation of acrolein or an acrolein precursor to form acrylic acid, which effluent gas contains acrolein, which method comprises:

passing said effluent gas at a temperature of from 100° to 300° C. into the base of a fractionation tower wherein said effluent gas is intimately contacted with a descending stream of liquid in said fractionation tower; removing a liquid bottoms stream consisting essentially of crude aqueous acrylic acid from the base of said fractionation tower; drawing off a portion of said liquid bottoms stream as said crude acrylic acid product; recycling the remainder of said bottoms stream as a liquid recycle to upper portions of said fractionation tower; and removing overhead vapors from said fractionation tower comprising a predominant portion of the acrolein contained in said effluent gas; said descending stream of liquid which is intimately contacted with said effluent gas being at a temperature which is within 15 Centigrade degrees of but does not exceed the dew point of said effluent gas at the pressure maintained at the base of said fractionation tower, said overhead vapors being withdrawn from said fractionation tower at a temperature within the range of 0° to 40° C. and said liquid recycle being at a temperature substantially less than the temperature of said liquid bottoms stream.

* * * * *